United States Patent [19]

Gold et al.

[11] Patent Number: 5,230,902
[45] Date of Patent: Jul. 27, 1993

[54] UNDENATURED WHEY PROTEIN CONCENTRATE TO IMPROVE ACTIVE SYSTEMIC HUMORAL IMMUNE RESPONSE

[75] Inventors: Phil Gold, Westmount; Gustavo Bounous, Montreal; Patricia A. L. Kongshavn, St. Lambert, all of Canada

[73] Assignee: Immunotec Research Corporation, Montreal, Canada

[21] Appl. No.: 563,794

[22] Filed: Aug. 3, 1990

Related U.S. Application Data

[63] Continuation of Ser. No. 289,971, Dec. 23, 1988, abandoned, which is a continuation-in-part of Ser. No. 188,271, Apr. 27, 1988, abandoned.

[51] Int. Cl.$^5$ .............................. A61K 35/20
[52] U.S. Cl. .................. 424/535; 514/2; 530/365; 530/833
[58] Field of Search .......... 514/2, 21, 251, 276, 514/885; 530/365, 833; 424/535; 426/72

[56] References Cited

U.S. PATENT DOCUMENTS

| | | | |
|---|---|---|---|
| 4,710,387 | 12/1987 | Uiterwaal et al. | 726/72 |
| 4,753,926 | 6/1988 | Lucas et al. | 514/251 |
| 4,784,685 | 11/1988 | Meister | 71/106 |

FOREIGN PATENT DOCUMENTS

| | | |
|---|---|---|
| 1136919 | 7/1982 | Canada . |
| 0022696 | 1/1981 | European Pat. Off. . |
| 239722 | 10/1987 | European Pat. Off. . |
| 2296428 | 9/1976 | France ................... 514/21 |
| WO87/4050 | 7/1987 | PCT Int'l Appl. . |
| 1495940 | 12/1977 | United Kingdom .......... 424/95 |

OTHER PUBLICATIONS

Horwitt, M. K. in *The Vitamins*, 2d ed., vol. V, Academic Press, New York, 1972, pp. 88–96.
Jansen, B. C. P. in *The Vitamins*, 2d ed., vol. V., Academic Press, New York, 1972, pp. 156–164.
Bounous et al. J Nutr 112(9):1747–1755 (1982).
Bounous et al. J Nutr 113:1415–1421 (1983).
Bounous et al. J Nutr 115(11):1409–1417 (1985).

*Primary Examiner*—Douglas W. Robinson
*Assistant Examiner*—Jean C. Witz
*Attorney, Agent, or Firm*—John P. White; Craig J. Arnold

[57] ABSTRACT

This invention provides a method of improving the humoral immune response or increasing the concentration levels of glutathione in mammals, which comprises administering orally to a mammal a therapeutically or a prophylactically effective amount of undenatured whey protein concentrate which has a biological activity based on the overall amino acid and associated small peptides pattern resulting from the contribution of all its protein components. A method for improving the humoral immune response in mammals also is disclosed which comprises administering orally to a mammal the combination of a vitamin supplement containing vitamin $B_2$ in an amount in excess of minimum daily requirements and an effective amount of undenatured whey protein concentrate. This invention further provides a dietary supplement for a mammal which comprises an effective amount of vitamin $B_1$, and $B_2$ and a therapeutically or prophylactically effective amount of whey protein supplement.

16 Claims, 9 Drawing Sheets

C = CONTROL; CASEIN DIET FED AND PURINA FED ARE POOLED
W = WHEY

UNDENATURED WHEY PROTEIN CONCENTRATE TO IMPROVE ACTIVE SYSTEMIC HUMORAL IMMUNE RESPONSE

RELATED APPLICATION

This application is a continuation of U.S. application Ser. No. 289,971, filed Dec. 23, 1988, now abandoned, which is a continuation in part of U.S. application Ser. No. 188,271 filed Apr. 27, 1988, now abandoned.

1. AREA OF INVESTIGATION

Effect of dietary whey protein on the immune response to sheep red blood cells, host resistance to bacterial infections, development of tumors, and the process of aging.

Whey and whey protein have been utilized from time immemorial for nutritional purpose. In addition, whey was recommended in folk and ancient medicine for the treatment of various diseases and, in one instance, lifetime feeding of hamsters with a whey protein diet has been shown to promote longevity with no explanation given. We have shown, in controlled experiments, for the first time, that whey protein feeding specifically enhances mice immune response to sheep red blood cells (SRBC), resistance to pneumococcal infection, inhibits the development of colon cancer and delays the process of aging independently of its nutritional quality.

The search for the possible mechanism of immunoenhancement by whey protein feeding has revealed to us the provocative possibility that whey protein may contribute to a broader biological effect of a protective nature involving susceptibility to cancer, diseases of aging and general detoxification of environmental agents. All these conditions appear to be somehow related to changes in glutathione which is a ubiquitous element exerting a protective effect against superoxide radicals and other toxic agents. Our studies have shown that the observed enhancement of the immune response is associated with greater production of splenic glutathione in immunized mice fed whey protein in comparison to mice fed a casein or cysteine enriched casein diet. The efficiency of dietary cysteine in inducing supernormal glutathione levels is greater when it is delivered in the whey protein than as free cysteine. Glutathione was found at higher levels in the heart and liver of whey protein fed old mice in comparison to mice fed the corresponding casein diet or Purina Mouse Chow. In old mice dietary whey protein was found to delay the onset of the diseases of aging.

2. DEFINITIONS (a) Whey Protein:

Whey proteins are the group of milk proteins that remain soluble in "milk serum" or whey after precipitation of caseins at ph 4.6 and 20° C. The major whey proteins in cow's milk are beta-lactoglobulin ($\beta$L), alpha-lactalbumin ($\alpha$L), immunoglobulin and serum albumin (SA) in order of decreasing amounts.(7)

(b) C=casein;

(c) SRBC=Sheep red blood cells;

(d) PFC Plaque forming cells (spleen): enumeration of PFC in spleen is used to assess the humoral immune response to SRBC injection;

(e) GSH Glutathione ($\gamma$-glutamyl-cysteinyl-glycine); and (f) Unless otherwise specified, the defined formula diets tested varied only in the type or protein.

(g) Whey of bovine milk contains approximately 6 g per liter protein, most of the lactose, mineral and water soluble vitamins.

A suitable source of whey protein concentrate is the material known by the trade mark PROMOD, which is a protein supplement provided in powder form by Ross Laboratories, a Division of Abbott Laboratories U.S.A. This is a concentrated source of high quality protein which is useful for providing extra protein to persons having increased protein needs, or those who are unable to meet their protein needs with their normal diet. It contains whey protein concentrate and soy lecithin. It has the following nutrients:

| NUTRIENTS: | Per 5 g Protein (one scoop) | |
|---|---|---|
| Protein | | 5.0 g |
| Fat | Does not exceed | 0.60 g |
| Carbohydrate | Does not exceed | 0.67 g |
| Water | Does not exceed | 0.60 g |
| Calcium | Does not exceed | 23 mg (1.15 mEq) |
| Sodium | Does not exceed | 13 mg (0.57 mEq) |
| Potassium | Does not exceed | 65 mg (1.66 mEq) |
| Phosphorus | Does not exceed | 22 mg |
| Calories | | 28 |

It has the following typical amino acid composition per 100 g protein. 100 g PROMOD protein yields approximately 105 g of aminoacids.

| TYPICAL AMINO ACID COMPOSITION Per 100 g Protein Essential | |
|---|---|
| Amino Acids: | Histidine, 1.9 g; |
| | Isoleucine, 6.2 g; |
| | Leucine, 10.8 g; |
| | Lycine, 9.3 g; |
| | Methionine, 2.2 g; |
| | Phenylalanine, 3.6 g; |
| | Threonine, 7.3 g; |
| | Tryptophan, 1.9 g; |
| | Valine, 6.0 g. |
| Non-Essential Amino Acids: | Alanine, 5.3 g; |
| | Arginine, 2.6 g; |
| | Aspartic Acid, 11.2 g; |
| | Cysteine, 2.6 g; |
| | Glutamic Acid, 18.2 g; |
| | Glycine, 2.1 g; |
| | Proline, 6.5 g; |
| | Serine, 5.6 g; |
| | Tyrosine, 3.4 g. |

Diets

The concentration of some vitamins in the defined formula diet used in (most of) our experiments is given in Table 1 (Diet 1). Diets are prepared in the following way: 20 g of selected pure protein, 56 g of product 80056 protein free diet powder (Mead-Johnson Co. Inc., U.S.A.), 18 g cornstarch, 2 g wheat bran; 0.05 g Nutramigen vit-iron premix (Bristol-Myers, Ontario, Canada), 2.65 g KCl; 0.84 g NACl. Unless otherwise specified, the only variable in the various purified diets was the type of protein

3. PREVIOUS WORK

Dairy products are widely used as a good source of nutrition. In addition claims have been made to the effect that fermented wholemilk (yogurt) is beneficial in the management of some types of intestinal infections.

Certain dietary regimen based on ill defined cultured dairy products are said to be associated with long life expectancy in some regions of the USSR (Georgia etc).

Since time immemorable, serum lactis, latin for milk serum or whey, has been administered to the sick for the treatment of numerous ailments. In 1603 Baricelli(7) reported on the therapeutic use of cow or goat milk serum, sometimes mixed with honey or herbs. The spectrum of illness treated with whey included jaundice, infected lesions of the skin, those of the genito-urinary tract with purulent secretions, gonorrhea, epilepsy, quartan fever and other febrile states of different origins. Indeed, the common denominator of most of these illnesses appears to be a septic condition. Although physicians of both Ancient Times and of the Middle Ages agreed that whey treatment should be carried out over a period of several days, a difference of opinion appeared to exist concerning the daily amount prescribed. Thus, Galen, Hippocrates and Dioscoride insisted on a minimum daily amount of two 12 oz latin libras, and up to five libras a day according to gastric tolerance. This would represent between 1 to 2 liters of whey a day. Baricelli, on the other hand, reflected the trend of his times, limited the amount prescribed to one libra a day, given in fractionated doses on an empty stomach.

In the following year, Costaei(7) wrote about the virtues of whey in the treatment of several unrelated syndromes including broncopneumonitis and diarrhea with high fever. Unfortunately, in his long dissertation, the author fails to clearly discriminate between milk and milk serum treatment.

Since then, numerous articles published in Europe throughout the 17th, 18th and 19th centuries have advocated the therapeutic use of whey. In an Italian textbook published in the middle of the 19th century, at the dawn of scientific medicine, an interesting distinction is made between whole milk and milk serum. Milk is recommended firstly as a nutrient especially in patients with strictures of the gastrointestinal tract. In this respect the author emphasizes that the benefits of the then popular "milk therapy" of cachexia and tuberculosis are due only to the nutritional property of milk. Secondly, milk was prescribed in the treatment of poisoning because milk components would presumably neutralize ingested toxic material. Thirdly, milk therapy was suggested for the alleged capacity of this fluid to coat and sooth ulcers of the gastrointestinal tract.

Milk serum, on the other hand, was advocated in treatment of pneumonitis, acute inflammatory diseases of the intestines and urogenital tract, in spite of its recognized lower nutritional quality. Finally the author emphasized the ineffectiveness of whey in the treatment of disorders of the nervous system.(7)

The prime difference between whey, (serum lactis) and whole milk is the near absence in the former of the caseins, the casein-bound calcium and phosphate, most of the fat and fat soluble vitamins. The actual concentration in whey of "whey proteins" is only about 5% higher than that in milk. Hence quantitative differences between whey and milk could not be construed to represent a key factor in the alleged therapeutic effect of whey treatment because, if any, they imply the lack, in whey, of some important nutrients. Our data (7,14) may provide a scientific background to the presumed benefit of intensive treatment with "serum lactis".

We have shown the importance of the characteristic amino acid profile of whey protein concentrate in the immune enhancing effect of WPC. The caseins represent 80% of the total protein content of cow's milk while WPC is only 20%. Hence, it is conceivable that it is the separation of WPC from the caseins in whey which represents the crucial qualitative change, since this will render the amino acid profile of whey proteins unaltered by that of the caseins, once the digestive process has released free amino acids from all ingested proteins.(7)

Although no clinical trials have been reported, some interesting information can be gathered from data on human subjects.

Whey Protein in Neonatal Nutrition

Infant feeding studies indicate that whey predominant formulas are metabolically superior to casein predominant formulas (8, 9) in preterm babies.

Longevity

Studies performed at the Eppley Cancer Center in Nebraska (10, 11) showed that survival (resistance to spontaneous diseases) of female and male hamsters, measured over a 20 week period of feeding from 4 weeks of age, was best with 20 g/100 g (grams per hundred grams) WPC diet, in comparison with a 20 g/100 g methionine and cysteine supplemented casein diet. Body weight gains were similar in both groups. In lifetime feeding studies, the mean and maximal longevity of female and male hamsters fed 10, 20 and 40 g WPC/100 g diet was increased in comparison with those fed commercial laboratory feed (estimated 24% protein from various sources). Survival was best with the 20% WPC diet; in males, longevity increased by 50%. No significant relationship was noted between food intake, maximal weight and longevity.

4. OUR STUDIES

Our interest in the effect of amino acid intake upon the immune system was prompted by an observation made several years ago (1). We fed mice a defined formula diet containing a free amino acid mixture acid mixture duplicating casein. Another group of mice was fed a similar diet but with moderate restriction of phenylalanine and tyrosine compensated by a corresponding increment in the non-essential amino acid mixture. The second group of mice gained weight at the same rate as the mice fed the casein equivalent mixture of Purina mouse chow. However, when challenged with sheep red blood cells, these mice produced more antibodies and plaque forming cells against sheep red blood cells than Purina or casein equivalent-fed mice.

A new concept thus emerged, namely, that changes in the amino acid profile of the diet can influence the immune response independently of any systemic effect on the nutritional status of the host. But, more importantly, changes in the amino acid profile, i.e. protein type, could conceivably enhance the humoral immune response beyond that which had traditionally been considered to represent a "normal" response.

We subsequently assessed the effect on the immune response of different types of proteins in nutritionally adequate diets. Mice fed formula diets containing 20% or 28% lactalbumin (WPC) were found to produce more plaque forming cells to sheep red blood cells than mice fed Purina mouse chow containing about 22% protein from various sources and of similar nutritional efficiency. The immune enhancing effect of lactalbumin was maximal at 20% concentration (2). A 20 g net protein/100 g diet provides a good method to assess the effect of protein type on the immune system. At this level most protein supplies the minimum daily requirement of all indispensible amino acids for the growing mouse and this is important because the amino acid distribution, and not adequacy, is the variable under investigation.

In subsequent studies we have compared the effect of dietary lactalbumin (whey protein) to that of other purified proteins in formula diets of similar nutritional efficiency. The effect of graded amounts of dietary lactalbumin (L), casein (C), soy (S), wheat (W) protein and Purina rodent chow (stock diet) on the immune responsiveness of C3H/HeN mice has been investigated by measuring the specific humoral immune response to sheep red blood cells (SRBC), and hosts red blood cells (HRBC). The nutritional efficiency of these diets was normal and similar.

The immune response of mice fed the WPC diets, was found to be almost five times higher than that of mice fed the corresponding C diets. The humoral immune response of mice fed C, S, and W diets was substantially lower than that of mice fed stock diet, whereas that of mice fed L diet was higher. The above-described immune effect of all tested proteins was obtained at 20 g/100 g concentration with no further increments with 30- and 40 g/100 g protein in the diet.(4)

Because L [whey protein (w.p.)] was tested in comparison to a limited number of proteins, we could not ascertain at that time whether the enhancement of the humoral immune response observed in five (5) unrelated strains of mice fed a whey protein diet, was due to a real immunoenhancement, in absolute terms, by whey protein feeding or immuno-depression by the other food protein tested.

Indeed, we can now state, in retrospect, that these few purified food proteins (casein, soy and wheat) used as "control" for the whey protein mixture were immunosuppressive when compared to all of the other purified food protein subsequently tested, though nutritionally adequate and similar at 20% concentration in diet.

In fact, we subsequently tested whey protein against most commercially available purified food protein (casein, soy, wheat, corn, egg white, beef, fish protein, gamma globulin, beta-lactoglobulin, alpha-lactalbumin, serum albumin, spirulina maxima or scenedesmus algae protein) and found that indeed mice fed whey protein exhibit the highest immune response to foreign antigen (SRBC) (12) (FIG. 1). These proteins are nutritionally similar and adequate at the 20 g/100 g diet concentration (Table 2).

We have concluded that our newly discovered immune enhancing and host resistance promoting property of whey protein which we wish to protect by patient is not related to the already known nutritional quality of this protein. In fact, the nutritional property of whey protein at 20 g protein per 100 g diet concentration as used in our experiment is similar to that of the other proteins tested.

BRIEF DESCRIPTION OF THE DRAWINGS

In the drawings which form a part of this specification.

As shown in reference 3 of the attached list of references showing current and previous work, it can be demonstrated that although no significant differences in body growth are seen between the 12% whey protein (lactalbumin) and 28% whey protein diets, a dramatic enhancement of the immune response is noted with the 28% whey protein diet, unlike what happens with the casein diet where increasing the protein content from 12% to 28% influences neither body growth nor the immune response. In fact, we have found that the improved results appear to reach a plateau at about 20%. FIG. 3 of the drawings illustrates the effect. In FIG. 3 there is shown the effect of 3 weeks of dietary treatment with lactalbumin (whey protein) hydrolysate (open bars) or casein hydrolysate (hatched bars) on the number of plaque-forming cells (PFC) per spleen 5 days after immunization with $5 \times 10^5$ sheep red blood cells. Each value represents the means of 10 mice±SEM. 28% L diet vs. 12% L diet: $P \leq 0.01$ by Student's t-test. By the two-way analysis of variance (F test) for both strain of mice, the effect of the quality of protein (L vs. C) is highly significant, $P \leq 0.001$.

As shown in reference 12 on the list, it is clear that despite great differences in immune response to SRBC no difference is seen in food consumption, final weight, and serum proteins among mice fed the various purified proteins at 20 g/100 g diet concentration. (See Table 2).

In Table 2, in reference 3, data are presented on the nutritional efficiency of the different diets. Mice fed Purina chow and the 12 or 28% C and L diets increased in body weight by approximately the same amount with similar food consumption ranging from 3.5 g to 3.8 g/24 hours. No significant differences were observed between dietary groups in serum protein values and white cell counts (data now shown).

We made the interesting observations that the delayed occurrence of spontaneous death in mice fed the whey protein diet in comparison to those fed the casein diet or Purin (Table 7), is not associated with any deference in food consumption of body weight among the three dietary groups (Table 8).

Figure 1:
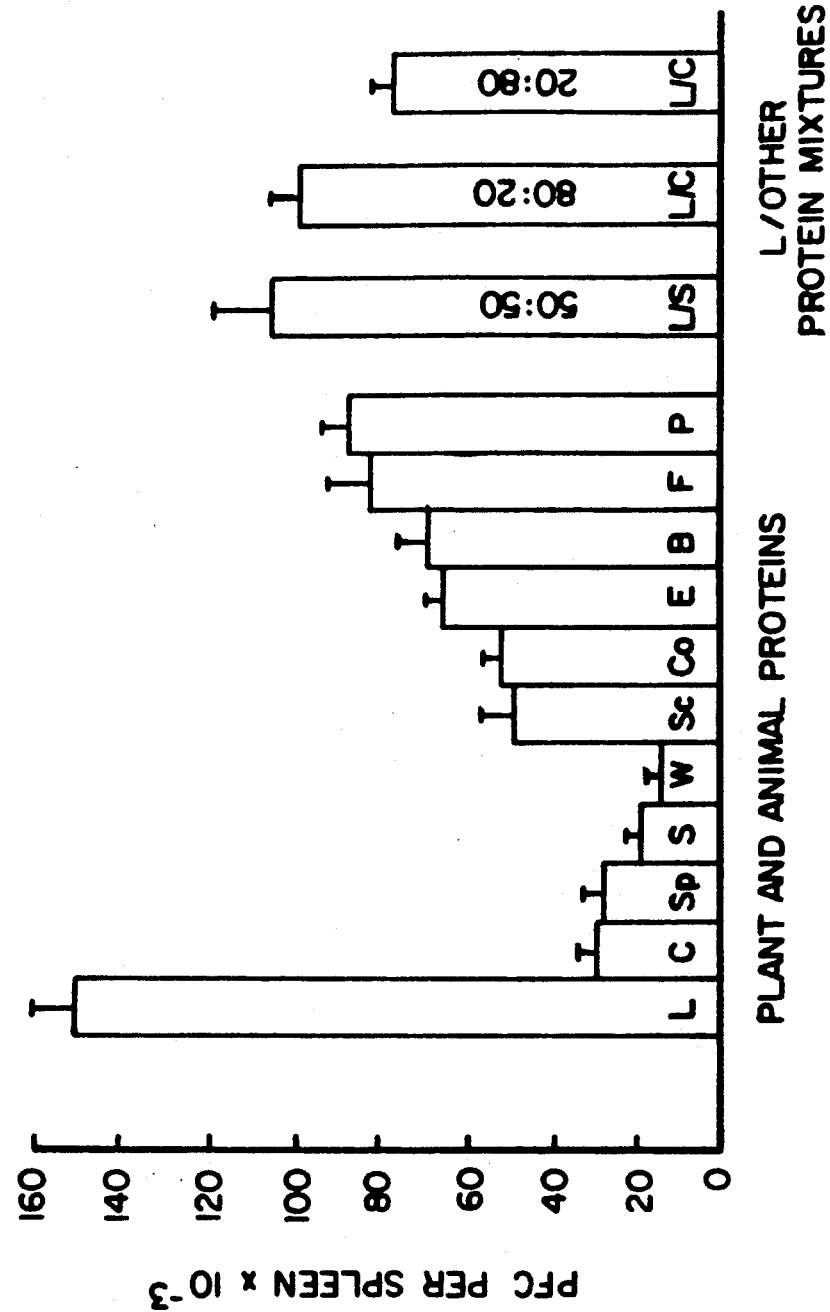
FIGS. 1 and 2 show plaque forming cells-spleen (PFC) on the day showing peak production of pfc following immunization with SRBC.

FIG. 1 shows plaque forming cells-spleen (PFC) on the day showing peak production of PFC following immunization with $10^6$ SRBC. Effect of 2 weeks of dietary treatment with 20 g/100 g diet of either lactalbumin (L), casein (C), Spirulina maxima protein (Sp), soy protein (S), wheat protein (W), Scenedesmus protein (Sc), corn (Co) protein, egg albumin (E), beef protein (B), fish protein (F), Purina mouse chow (P), or 20 g/100 g diet of a mixture containing 50% L and 50% S (L/S), or 80% L and 20% C, or 20% L and 80% C (L/C). Each value represents the mean±SD. See text (reference 12) for statistical significance of differences. L=whey protein concentrate.

Figure 2:
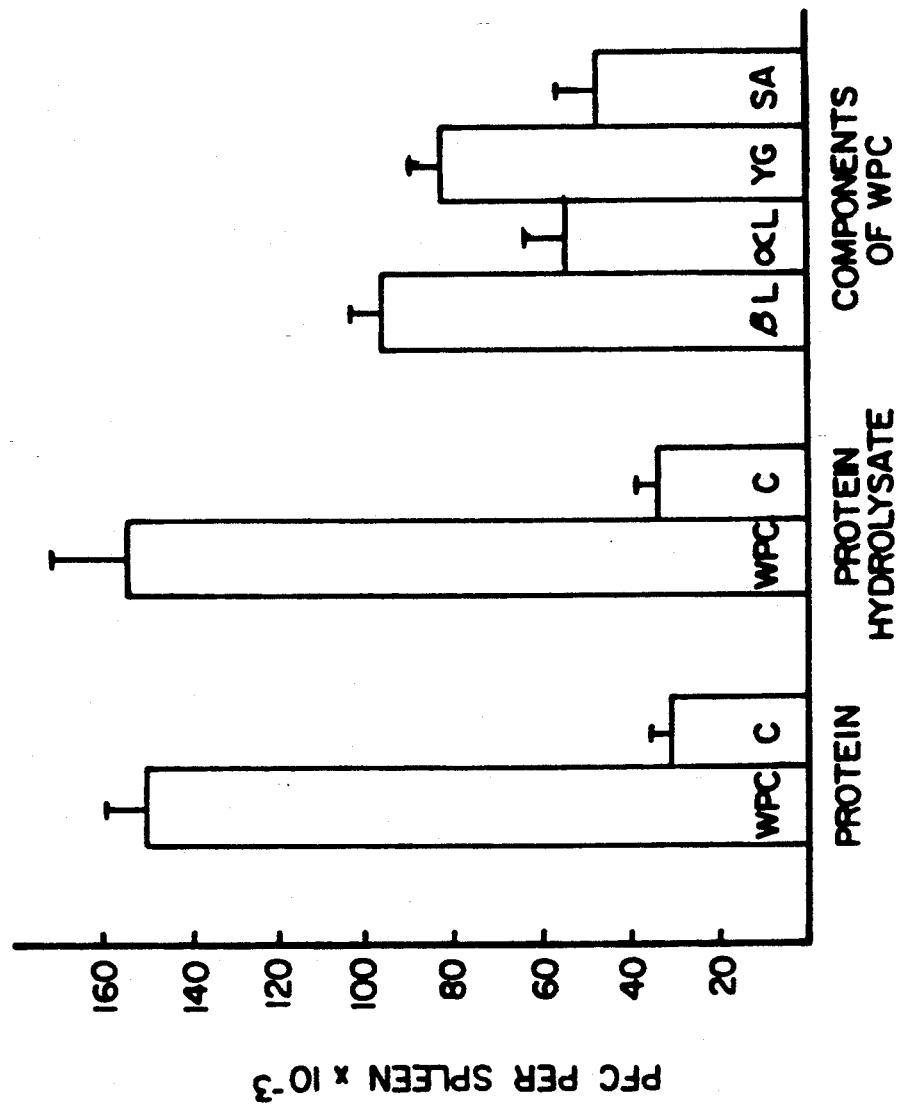
Figure 3:
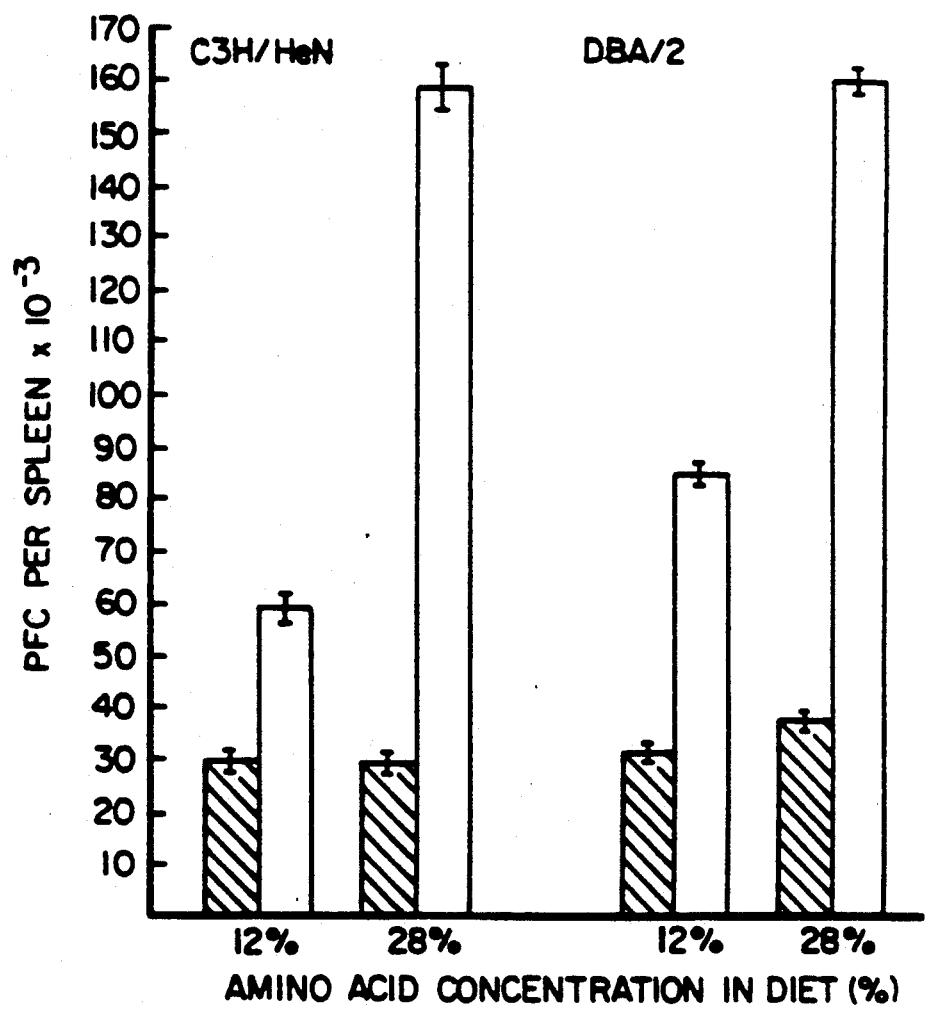
FIG. 3 shows increased immune response noted with a 28% whey protein diet.

FIG. 2 shows plaque forming cells/spleen (PFC) on day showing peak production of PFC following immunization with $10^6$ SRBC. Effect of 3 weeks of dietary treatment with 20 g/100 g diet of either whey protein concentrate (WPC), casein (C), whey protein concentrate hydrolysate, casein hydrolysate, beta-lactoglobulin ($\beta$L), alpha-lactalbumin ($\alpha$L), gamma-globulin ($\gamma$G) or bovine serum albumin (SA). Each value represents the Mean ±SD.

Factors Responsible for the Immunoenhancing Effect of Whey Protein in Diet

Our studies show that the immunoenhancing effect of WPC in comparison to C is maintained when these two proteins are replaced in formula diets by a pancreatic hydrolysate (free amino acid and oligo peptides with MW less than 100) (FIG. 2) (7,12). Our results also indicate that mice fed diets containing any one of the four major protein components of the WPC mixture developed a PFC response to SRBC inferior to that of mice fed the corresponding whey protein mixture. We can thus conclude that the observed immunoenhancing effect of WPC is dependent upon the contribution of all its protein components.

For these reasons we can assume that this phenomenon is not related to milk protein allergy or some other manifestation of oral immunization.(14)

Mechanism Responsible for the Immunoenhancing effect of Whey Protein in Diet

Over the past few years we have attempted to identify the changes induced by dietary protein type which might directly or indirectly affect the humoral immune responsiveness. In mice not challenged with an immunogenic stimulus, the type of protein in the diet was found to have little or no effect on a variety of parameters examined. Thus, body growth, food consumption, serum protein, minerals and trace metals, circulating leukocytes and more specifically, the genesis of bone marrow B lymphocytes were all within normal limits (3-7). These findings confirm that a 20 g/100 g diet concentration, the proteins provide an adequate daily supply of essential amino acid for the growing mice. The only significant effect of protein type was found to be in change in plasma amino acid profile, which essentially conformed to the amino acid composition of the ingested protein, with the notable exception of cysteine. (Tables 3, 4).

We were particularly intrigued by the finding that, in spite of an 8-fold higher cysteine content in SPC, the plasma level of cysteine in WPC diet-fed mice was not different from that in their C diet-fed counterparts. The fate of the excess cysteine was a matter of interest. Dietary cysteine is a rate limiting substrate for the synthesis of glutathione (GSH) which is necessary for lymphocyte proliferation. The redox state of the lymphocyte can modulate the intracellular concentration of cyclic GMP, which is known to be intimately involved in lymphocyte proliferation.

Figure 4:
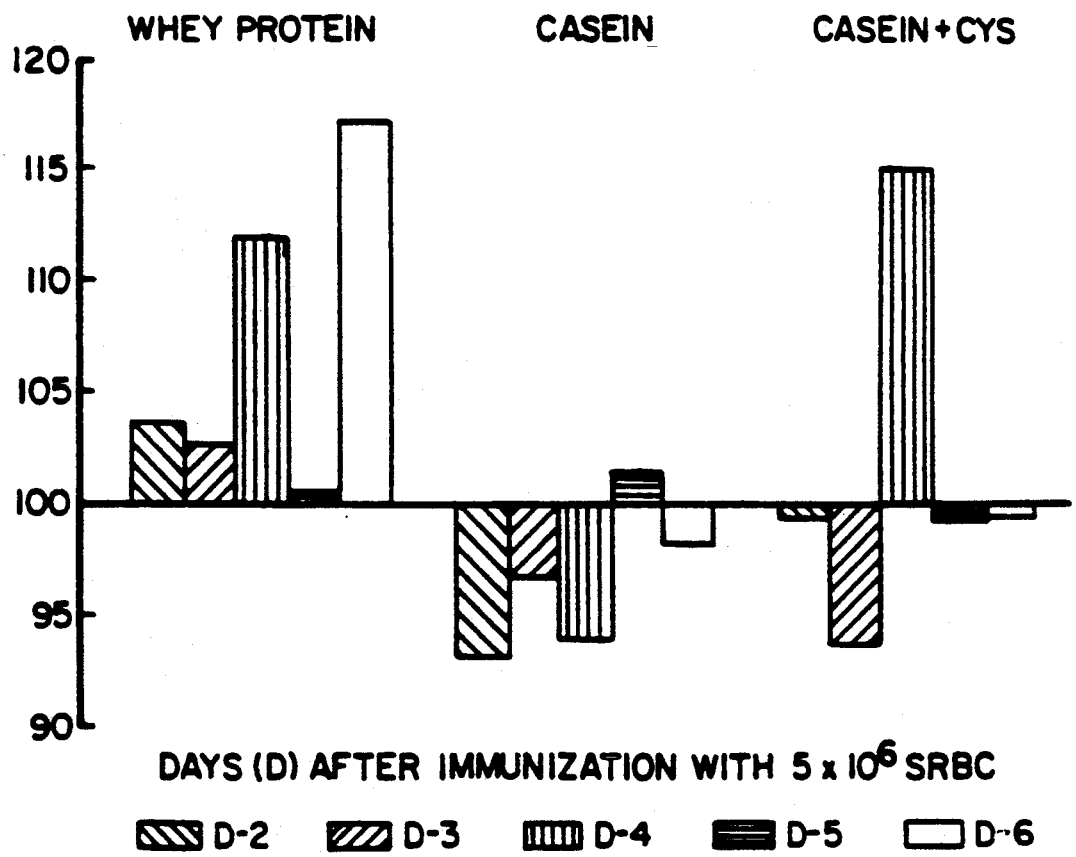
FIG. 4 shows the effects of whey protein on GSH, following immunization with SRBC (14).

Our studies have shown that the observed enhancement of the immune response is associated with greater production of splenic glutathione in immunized mice fed whey protein in comparison to mice fed a casein or cysteine enriched casein diet. The efficiency of dietary cysteine in inducing supernormal glutathione levels is greater when it is delivered in the whey protein than as free cysteine (14) (See FIG. 4).

The search for the possible mechanism of immunoenhancement by whey protein feeding has revealed to us the provocative possibility that whey protein may contribute to a broader biological effect of a protective nature involving susceptibility to cancer, diseases of aging and general detoxification of environmental agents. All these conditions appear to be somehow related to a drop in glutathione which is a ubiquitous element exerting a protective effect against superoxide radicals and other toxic agents.

Increased heart and liver GSH levels were observed in old C-57 BL/GNIA mice fed the whey protein (WP) diet in comparison to mice fed the equivalent C diet or Purina Mouse Chow. (FIG. 5, 6), (reference 16)

In conclusion we have demonstrated that in all the experimental situations above described the immune enhancing effect of whey protein does not depend upon its nutritional property.

Dietary Whey Protein and Bacterial Infection

Because our studies had shown that dietary protein type influences the humoral immune response, we then proceeded to investigate the effect of WC in diet on the resistance of mice to pneumococcal infection. Acquired immunity to this infection is largely dependent on the humoral immune response. C3H/He3 mice fed a diet containing 20 g WPC/100 g diet showed improved survival after i.v. infection with Streptococcus pneumoniae type 3 as compared to mice fed a 20 g C/100 g diet of similar nutritional efficiency (7) (Table 5).

On the basis of our various studies, it was shown that the enhanced resistance of mice fed the whey protein diet to infection with Streptococcus pneumoniae type 3 was independent of the weight of the animal at the time of infection and the weight gained before infection (animals were fed the diets for 2 weeks prior to infection). In this connection reference is made to reference 7 on the enclosed list at page 22 and elsewhere.

DIETARY WHEY PROTEIN AND EXPERIMENTAL TUMORS

We have recently observed that a 20 g WPC/100 g diet significantly inhibits the incidence and size of dimethylhydrazine (DMH) induced tumors in the murine colon in comparison to a 20 g C/100 g diet or Purina mouse chow of similar nutritional efficiency. This is a highly immunogenic type of tumors that develop after a long term exposure to the carcinogen. DMH-induced colon tumors appear to be similar to those found in humans as far as type of lesions and chemotherapeutic response characteristics are concerned. The described enhancement of the humoral immune response (heterologous erythorcytes) in WPC fed mice substantiate an immunological mechanism for the observed resistance of WPC fed mice to this immunogenic type of tumor (15) and Table 6.

It should be noted that the similarity of body weight curves among the three dietary groups (whey protein, casein diets and Purina) is consistent with studies in other mouse strains (2-7, 12-14). This effect is striking and appears to rule out conventional nutritional factors for the observed differences in the development of tumors. Reference is made to reference 15 on the enclosed list.

AGING

Tissue Glutathione (16)

Figure 5:
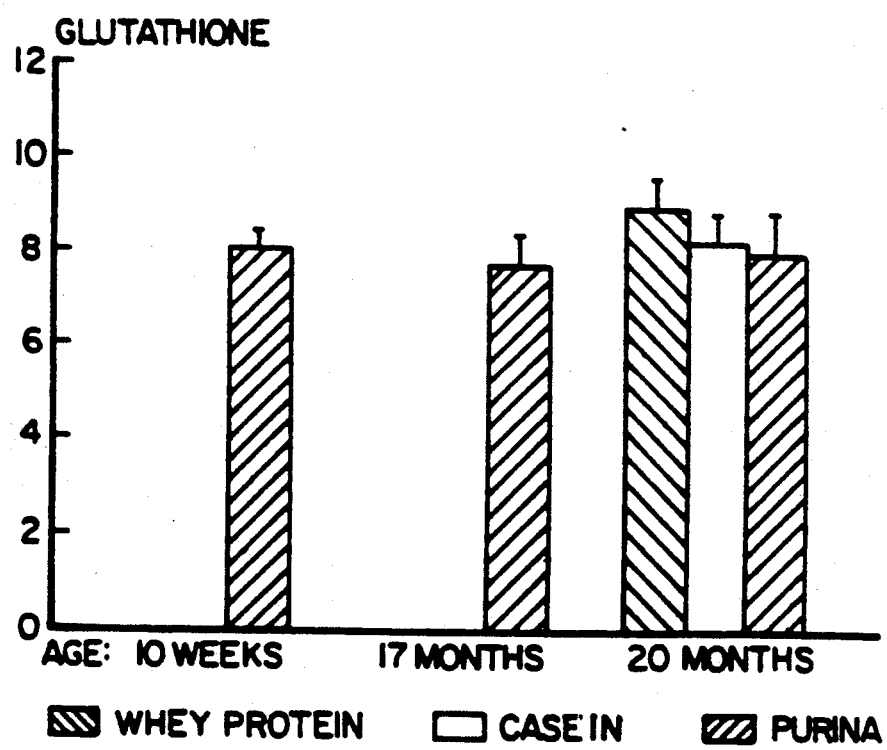
FIG. 5 and FIG. 6, respectively, show the heart and liver GSH levels which were observed in old C-57 BL/GNIA mice fed the whey protein (WP) diet in comparison with mice fed the equivalent C diet or Purina Mouse Chow.
Figure 6:
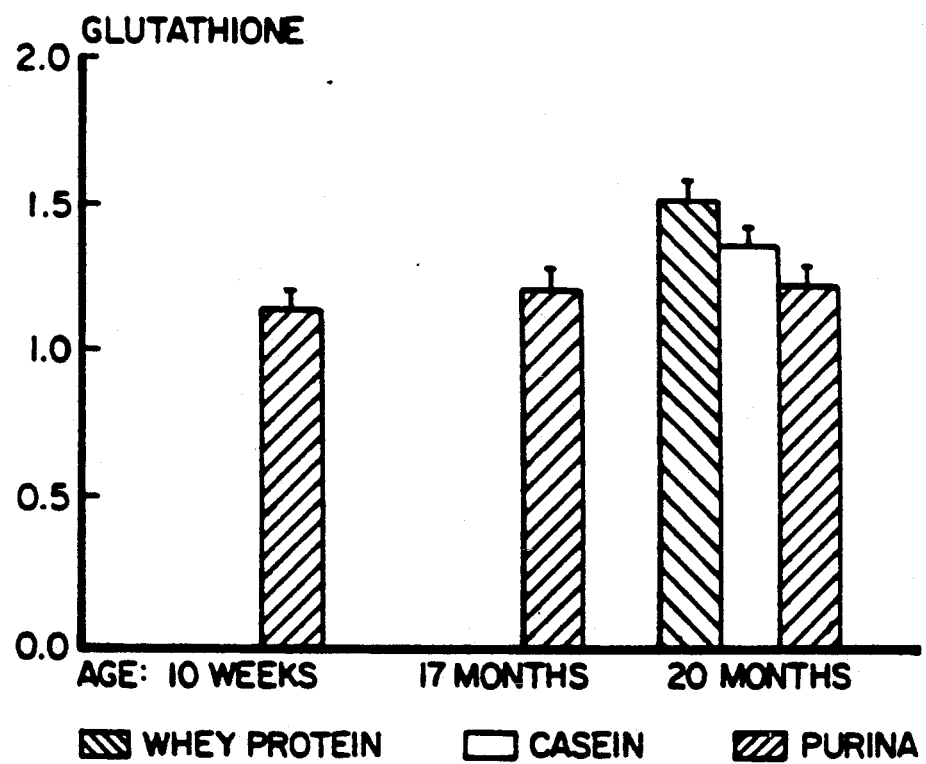

Male C57/BL/6N1A mice were fed ad libitum either 20 g whey protein/100 g diet, or 20 g casein/100 g diet or Purina mouse chow, from age 17 months until sacrificed three months later at age 20 months. GSH (glutathione) content was found to be higher in the liver and heart of whey protein fed mice in comparison to the casein-diet or Purina fed counterparts (FIGS. 5 and 6). The GSH values in heart and liver of mice fed Purina laboratory chow was almost identical at 17 and 20 months of age. Thus no age related decline is noticed during this period of time. Moreover, the GSH values, at 17 and 20 months of age, of Purina fed mice are similar to those of 10 week old mice. Indeed, the whey protein diet appears to enhance, after 3 months, the GSH content of heart and liver above "normal" values. The mean±SD body weight changes over the three month period, expressed as percentage of initial weight, of mice fed either the whey protein diet, casein diet or Purina diet was 98.90±17.7, 100.38±15.99 and 99.30±18.50, respectively. Thus no significant differences were noted in body weight between the various dietary groups. Food consumption was also familiar, varying from 3.4±0.3 g/24 hr in the whey protein diet group to 3.8±0.4 g/24 hr in the Purina fed mice.

Survival Studies (16)

Figure 7A:
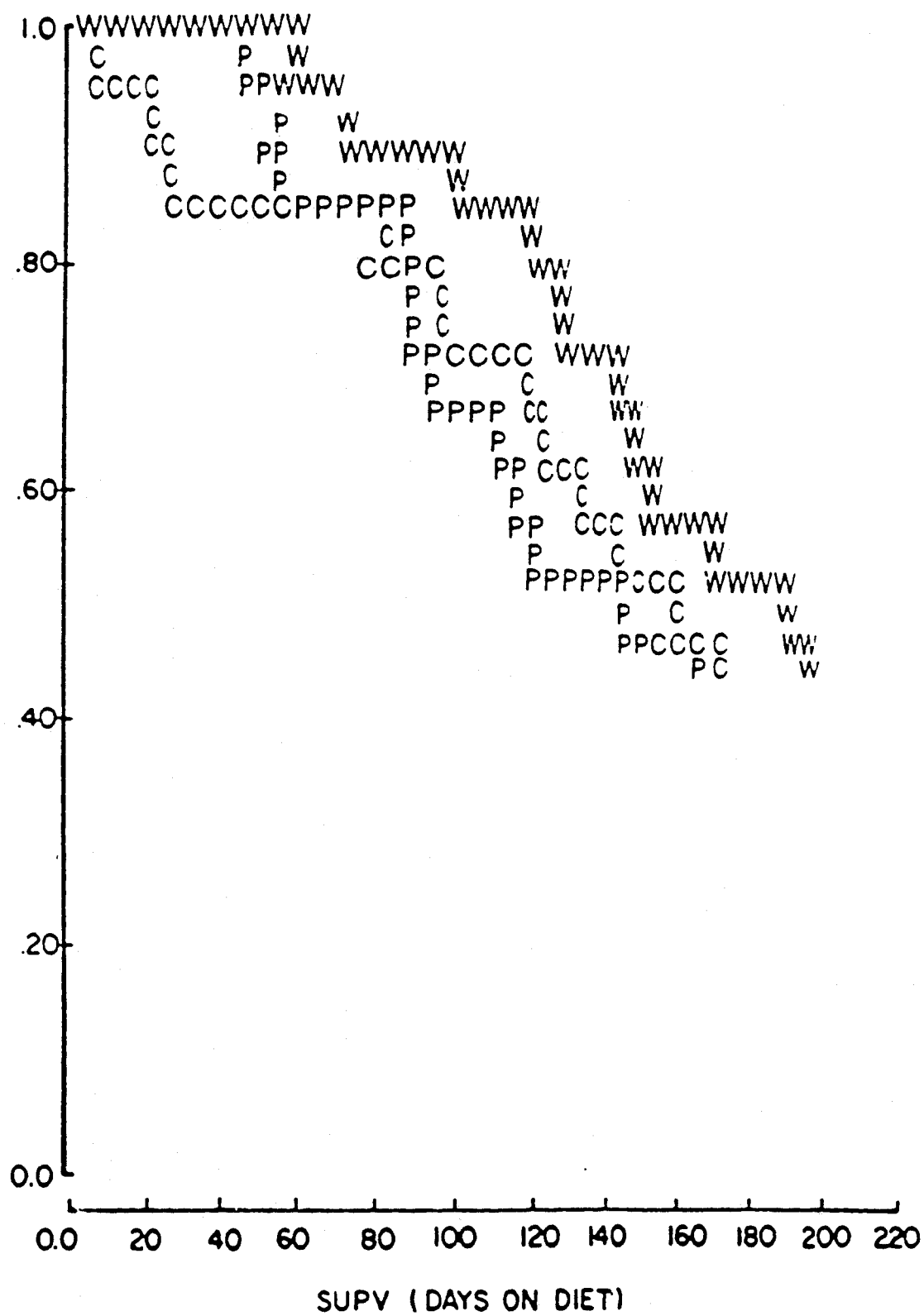
FIGS. 7A and 7B illustrates survival curves showing the relative mortality of mice fed Purina laboratory chow, casein and whey during a seven month period.
Figure 7B:
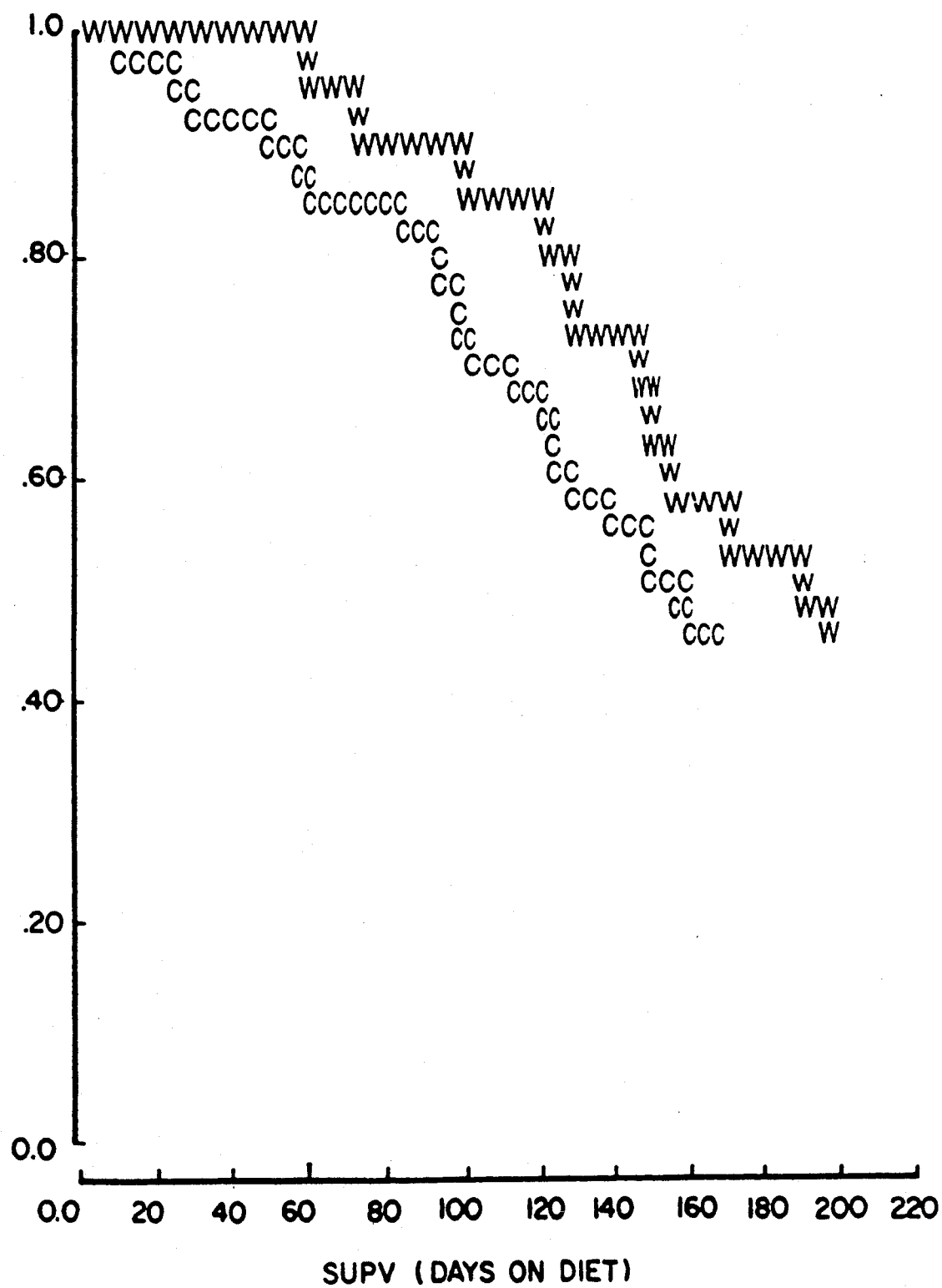

Male C57BL/6N1A mice fed ad libitum at the onset of senescense a 20 g wpc/100 g diet, in pathogen free environment, exhibit delayed mortality in comparison with mice fed Purina laboratory chow over a 7 month observation period extending from the age of 21 months (corresponding human age 55 years) to 28 months of age (corresponding human age to 80 years) at which time 55% mortality is reached. Mean survival time of mice fed the defined formula control diet differing from the whey protein diet only in the type of protein (20 g casein/100 g diet) is almost identical to that of Purina fed controls (FIG. 7), Table 7). NO significant difference is noticed amongst dietary groups in average body weight changes throughout the experiment (Table 8). Average food consumption in the whey protein-diet group was 2.8±0.4 g/24 hr and 3.0±0.4 g/24 hr in the casein-diet group. The greater amount of spillage of the Purina powder substantially hampers any realistic appraisal of food consumption in this particular group. Whereas other antioxidants, such as Vitamin E, have been shown to be effective primarily in animals that are abnormally deficient in antioxidant synthesis or absorption, dietary whey protein appear to represent an important element in promoting higher tissue GSH levels and in delaying the onset of the diseases of aging in normal wild-type animals. It is important to emphasize that in these longevity studies, the effect of whey protein on the diseases of aging and tissue glutathione is not related to the quality of whey protein as a nutrient which appears to be similar, at 20 g wpc/100 g diet concentration, to that of the other test proteins. A similar conclusion was reached in our previous studies on the effect of a whey protein diet on PFC response to SRBC, resistance to infections and development of tumors.

Synergistic Role of Vit. $B_2$, $B_1$ in the Immunoenhancing Effect of Dietary Whey Protein Concentrate In section 30 on page 13, page 14 and reference 14 are discussed the effect of whey protein on splenic cell GSH and the relationship between splenic GSH and PFC response to SRBC.

While whey protein represent an optimal source of cysteine, the rate limiting substrate for the biosyntheses of GSH, Vit. $B_2$ and $B_1$ are important element in the function of the GSH redox cycle.

Glutathione (GSH) status in tissues is maintained mainly in the reduced state (GSH:GSSG, 250), which is achieved by the efficient GSH peroxidase and reductase system coupled to the NADP+/NADPH redox pair. Endogenous toxic $H_2O_2$ is reduced to $H_2O$ through the oxidation of GSH to GSSG catalyzed by GSH peroxidase. At the expense of cellular NADPH, GSSG is effectively reduced back to GSH by NADPH:GSSG reductase, thus maintaining thiol balance. As a result, GSSG reductase has a great capacity to protect cells against oxygen toxicity from endogenous active oxygen species.

Vit. $B_1$ (thiamine) is involved in the transketolase reaction of the pentose phosphate shunt yielding NADPH and pentose.

Vit. $B_2$ (riboflavin): The coenzyme derivatives of riboflavin, flavin monomucleotide (FMN) and flavin adenin dinucleotide (FAD), are synthesized sequentially from riboflavin. Vit. $B_2$ deficient animals exhibit marked decreases in activities of FMN and FAD-requiring enzymes, such as GSH reductase.

In this sense it is conceivable that all these water soluble vitamins naturally present in whey, play an essential role for optimal function of the GSH redox cycle particularly when whey protein intake, as shown in our experiments, has produced higher level of GSH synthesis and storage in the tissues.

Figure 8:
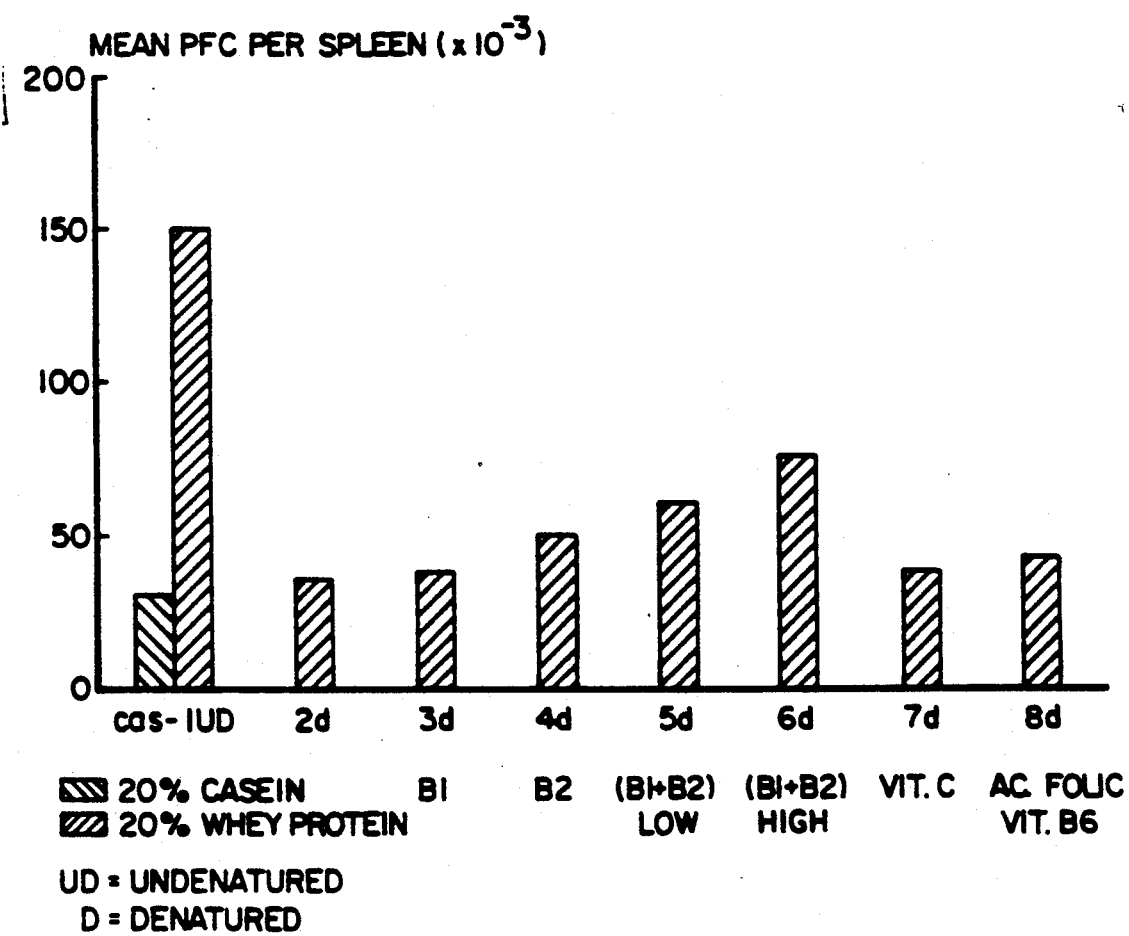
FIG. 8 shows the effect of 26 days dietary treatment on plaque forming cells (PFC) response to sheep red blood cells (SRBC) in mice fed diets with various levels of vitamines as indicated in Table 1.

Our studies (FIG. 8) shows that dietary levels of Vit. $B_1$, $B_2$ slightly above recommended allowance (Table 1, diets 5,6) significantly contribute to the immunoenhancing effect of dietary whey protein concentrate. Whey protein, by providing optimal bioavailability of the limiting substrate (cysteine) enhances the synthesis and storage of GSH. On the other hand, higher than normal intakes of Vit. $B_1$ and $B_2$ are necessary to maintain the GSH redox cycle at a level higher than normal, thus allowing the development of a better than normal immune response to SRBC. Individually the effect of each of the vitamins in whey protein fed mice is limited; however their synergistic effect on the immune response of whey protein fed mice is apparent (FIG. 8, diets 5,6 diet 1). The same vitamins are ineffective on the immune response of casein diet-fed mice. Although all these water-soluble vitamins are present in whey, it is interesting to note that the main natural source of the single most effective vitamin, riboflavin, is whey to which Vit. $B_2$ given its characteristic color.

In conclusion, dietary intake of Vit. $B_1$ and particularly $B_2$ above recommended daily allowance contribute to the development of enhanced immune response in whey protein fed animals: Vitamin $B_2+B_1$ appears to produce the strongest effect. When intake of these vitamins is at or slightly below these levels, body growth and animal appearance are normal, but the response to immune challenge is below the maximum potential of whey protein fed mice.

In the stomach, whey is separated from milk by the action of gastric juice. It is conceivable that the transit and absorption of the water-soluble vitamins and proteins of whey occur faster than those of the protein (casein) and vitamin constituents of the milk coagulum (curd). Hence the whey protein and vitamins including the vitamins $B_1$, and $B_2$ could enter the systemic circulation at a different rate than that of other milk constituents and express their synergistic effect on the immune system and the GSH redox cycle.

The immunoenhancing and the other specific biological properties of dietary whey protein described in this application, are heat labile and dependant upon the undenatured (native) state of the protein (which can also be affected by vigorous shaking, solvents, extreme ph changes, etc.) and are independent of its nutritional quality which is unaltered by the process of denaturation.

Unlike most other commercially available whey protein which are denatured, the whey protein used in our experiments, produced in Denmark (Lacprodan—80) is 90% undenatured (U.D. in FIG. 8). This protein displays the greatest tendency to denature under heat thus exposing its free sulfhydryl group (17). When experiments were done using a batch of w.p.c. received after a long surface transport from Denmark through the U.S. in exceptionally hot and humid weather (summer 1988), the immunoenhancing property of w.p.c. was lost (FIG. 8, 2d–8d). These experiments, while indicating the synergistic role of vit B, and B2, in the immunoenhancing effect of the diet, also show the negative effect of a presumably partially denatured whey protein. Previous studies have shown (14), that the immunoenhancing property of dietary whey protein is probably related to an optimal intracellular transport and availability f the cysteine which is a limiting precursor for glutathione synthesis. It is conceivable that partial denaturation of this protein had brought about the loss of its specific biological property by altering a cysteine bond crucial for intracellular transport of cysteine and GSH synthesis, without any effect on its nutritional quality.

In conclusion, the preparation of whey protein concentrate made as the "Danmark Protein" lacprodan-80 was produced before 1985 or in a comparable appropriate fashion, produced the biological activity sought. This activity correlates directly with the PFC essay employed in our experiments.

TABLE 1

| VITAMINS (mg/100 g Diet) | Vitamin Content of Test Diets | | | | | | |
|---|---|---|---|---|---|---|---|
| | REG. (Diet 1) | Diet 3 | Diet 4 | Diet 5 | Diet 6 | Diet 7 | Diet 8 |
| VIT. B1 | 0.34 | 1.42 | | 0.9 | 2.7 | | 1.0 |
| VIT. B2 | 0.38 | | 1.47 | 0.9 | 2.7 | | 0.6 |
| VIT. B6 | 0.26 | | | | | | 0.7 |
| AC. FOLIC | 0.063 | | | | | | 0.1 |
| VIT. C | 53.3 | | | | | 118.3 | |

TABLE 2

Effect of 19 days dietary regimen on food consumption, body growth, total serum protein and development of spleen.[h]

| Protein type | Avg. Consumption (g/mouse/day ± SEM)[a] | Initial Weight (g)[b] | Final Weight (% initial wt.)[c] | Serum Protein (g/100 ml)[d] | Averge Spleen Wt(mg)[3] | # cells(10^6) ± SEM[f] |
|---|---|---|---|---|---|---|
| Lactalbumin[j] | 2.8 ± 0.1 | 22.6 ± 0.6 | 118.0 ± 3.2 | 5.8 ± 0.2 | 117 ± 2.1 | 194 ± 4.0 |
| Casein | 2.9 ± 0.2 | 23.0 ± 0.8 | 117.8 ± 4.6 | 6.1 ± 0.3 | 113 ± 3.6 | 150 ± 4.1 |
| Spirulina maxima protein | 2.9 ± 0.3 | 19.8 ± 0.9 | 121.0 ± 1.8 | 5.4 ± 0.5 | 104 ± 3.4 | 138 ± 6.0 |
| Soy protein | 3.1 ± 0.2 | 21.2 ± 0.3 | 114.1 ± 1.3 | 6.0 ± 0.4 | 107 ± 3.8 | 144 ± 4.3 |
| Wheat protein | 2.9 ± 0.2 | 20.0 ± 0.3 | 115.0 ± 2.2 | 5.9 ± 0.3 | 109 ± 2.6 | 139 ± 8.0 |
| Scenedesmus protein | 3.1 ± 0.4 | 23.0 ± 0.3 | 113.0 ± 3.0 | 6.1 ± 0.1 | 107 ± 4.0 | 152 ± 10.0 |
| Corn protein | 3.1 ± 0.2 | 22.8 ± 1.1 | 115.5 ± 5.4 | 5.6 ± 0.2 | 118 ± 3.2 | 162 ± 7.0 |
| Egg albumin | 3.0 ± 0.1 | 20.7 ± 0.6 | 116.0 ± 2.9 | 5.8 ± 0.3 | 114 ± 3.0 | 157 ± 6.0 |
| Fish protein | 2.8 ± 0.4 | 20.9 ± 0.3 | 117.1 ± 1.3 | 5.5 ± 0.1 | 105 ± 2.4 | 152 ± 6.0 |
| Beef protein | 2.9 ± 0.4 | 22.0 ± 0.3 | 113.0 ± 1.9 | 5.7 ± 0.3 | 109 ± 1.8 | 150 ± 5.0 |
| Lactalbumin/Soy (50:50) | 2.9 ± 0.3 | 20.7 ± 0.5 | 121.0 ± 4.7 | 5.8 ± 0.5 | 110 ± 8.0 | 180 ± 7.0 |
| Lactalbumin/Casein (80:20) | 2.7 ± 0.4 | 23.6 ± 0.4 | 121.0 ± 2.0 | 5.6 ± 0.4 | 112 ± 4.0 | 148 ± 4.9 |
| Lactalbumin/Casein (20:80) | 3.0 ± 0.2 | 23.4 ± 0.5 | 116.0 ± 2.0 | 6.0 ± 0.3 | 118 ± 4.0 | 145 ± 5.0 |
| Nonpurified diet[g] | 3.2 ± 0.3 | 21.1 ± 0.5 | 114.7 ± 1.8 | 5.8 ± 0.2 | 114 ± 1.9 | 189 ± 6.0 |

[a]The average food consumption over the 18 days feeding period was not considered different by ANOVA.
[b,c,d,e,f]The average initial body weight (b), increase in body weight (c), total serum protein (d) and spleen weight (e) were not considered different by ANOVA. The numbers of cells per spleen (f) in lactalbumin and Purina fed groups were higher by ANOVA (p:0.0001) than the corresponding values in the casein, wheat, soy and fish protein groups.
[g]Purina mouse chow, Ralston Purina Company, St. Louis. MO., (estimated 22 g protein from various sources per 100 g diet).
[h]Mice received 5 × 10^6 SRBC on day 14.
[j]Lactalbumin = Whey Protein Concentrate.

TABLE 3

AMINO ACID COMPOSITION OF TEST PROTEINS[a] (g/100 g protein)

| AMINO ACID | CASEIN | WHEY PROTEIN CONCENTRATE |
|---|---|---|
| Phenylalanine | 5.3 ± 0.2 | 3.4 ± 0.3 |
| Tryptophan | 1.4 ± 0.2 | 2.1 ± 0.0 |
| Glycine | 2.0 ± 0.1 | 2.0 ± 0.2 |
| Serine | 6.2 ± 0.5 | 5.2 ± 0.4 |
| Leucine | 10.0 ± 0.4 | 10.4 ± 0.7 |
| Isoleucine | 6.0 ± 0.6 | 6.1 ± 0.8 |
| Valine | 7.1 ± 0.3 | 5.8 ± 0.8 |
| Methionine | 2.9 ± 0.2 | 2.1 ± 0.3 |
| Cysteine | 0.3 ± 0.1 | 2.3 ± 0.3 |
| Aspartic acid | 7.3 ± 0.1 | 10.7 ± 0.7 |
| Glutamic acid | 22.9 ± 0.3 | 18.8 ± 0.7 |
| Histidine | 3.0 ± 0.1 | 2.0 ± 0.2 |
| Tyrosine | 6.0 ± 0.1 | 3.0 ± 0.4 |
| Proline | 11.6 ± 0.4 | 6.1 ± 0.7 |
| Arginine | 4.0 ± 0.1 | 2.8 ± 0.3 |
| Alanine | 3.1 ± 0.3 | 4.9 ± 0.4 |
| Lysine | 8.2 ± 0.1 | 9.2 ± 0.5 |
| Threonine | 4.6 ± 0.3 | 6.8 ± 1.3 |

[a]Value expressed as Mean ± S.D. of data from reliable sources (Reference 13).

TABLE 4

EFFECT OF DIETARY PROTEIN TYPE ON PLASMA AMINO ACID PATTERNS

| Amino Acid | Lactalbumin 20 g % (whey protein concentrate) nmol/ml | Casein 20 g % | P-value |
|---|---|---|---|
| Isoleucine | 90 ± 5 | 95 ± 8 | — |
| Leucine | 125 ± 5 | 113 ± 4 | — |
| Valine | 232 ± 10 | 278 ± 13 | 0.025 |
| Methionine | 72 ± 3 | 92 ± 6 | 0.025 |
| Cystine | 37 ± 3 | 37 ± 3 | — |
| Phenylalanine | 51 ± 1 | 75 ± 4 | 0.0005 |
| Tyrosine | 55 ± 2 | 83 ± 5 | 0.005 |
| Threonine | 310 ± 7 | 223 ± 2 | 0.0005 |
| Tryptophan | — | — | — |
| Lysine | 301 ± 6 | 323 ± 7 | — |
| Histidine | 50 ± 1 | 64 ± 4 | 0.005 |
| Arginine | 61 ± 4 | 92 ± 6 | 0.005 |
| Glycine | 142 ± 7 | 144 ± 7 | — |
| Serine | 120 ± 8 | 132 ± 4 | — |
| Alanine | 437 ± 18 | 382 ± 19 | 0.05 |
| Proline | 52 ± 5 | 117 ± 10 | 0.0005 |
| Aspartic Acid | 24 ± 2 | 16 ± 1 | 0.005 |
| Glutamic acid | 65 ± 2 | 44 ± 4 | 0.005 |

Mean ± SD.

TABLE 5

SUSCEPTIBILITY TO TYPE 3 S. PNEUMONIAE OF THREE SERIES OF MICE FED DIETS OF VARIOUS PROTEIN TYPES[1]

| Days Post-Infection[2] | Experiment 1 C | Experiment 1 L | Ratio of alive:dead mice Experiment 2 C | Experiment 2 L | Experiment 3 C | Experiment 3 L |
|---|---|---|---|---|---|---|
| 0 ($10^2$) | 8:0 | 8:0 | 10:0 | 10:0 | 10:0 | 10:0 |
| 2 | 8:0 | 8:0 | 10:0 | 10:0 | 10:0 | 10:0 |
| 3 | 7:1 | 8:0 | 10:0 | 10:0 | 10:0 | 10:0 |
| 4 | 7:1 | 8:0 | 9:1 | 10:0 | 9:1 | 10:0 |
| 9 ($10^3$) | 7:1 | 8:0 | 9:1 | 10:0 | 9:1 | 10:0 |
| 11 | 7:1 | 8:0 | 9:1 | 10:0 | 9:1 | 10:0 |
| 12 | 7:1 | 8:0 | 5:5 | 9:1 | 8:2 | 10:0 |
| 13 | 6:2 | 8:0 | 4:6 | 9:1 | 8:2 | 10:0 |
| 14 | 5:3 | 8:0 | 4:6 | 9:1 | 7:3 | 9:1 |
| 40 | 5:3 | 8:0 | 4:6 | 9:1 | 7:3 | 9:1 |

[1]Mice were infected after 2 wk treatment with casein diet (C) (20 g casein/100 g diet), or lactalbumin diet (L) (20 g/100 g).
[2]Injected i.v. in 1% FCS-Ringer; 9 days after infection with $10^2$ pneumococci the surviving mice were infected with a dose of $10^3$ pneumococci.
C = Casein
L = Lactalbumin = Whey Protein Concentrate.
Overall mortality is 36% in the C fed groups and this is significantly higher (P = 0.002) than that of the L fed mice which is 7.1%.

TABLE 6

Effect of Dietary Protein Regimen on Body Growth and Tumor Development in 1,2-Dimethylhydrazine treated A/J mice[a].

| Variable | Whey Protein | Casein | Purina |
|---|---|---|---|
| Body weight[b] | | | |
| Initial(g) | 21.06 ± 1.32 | 23.94 ± 2.49 | 22.13 ± 1.36 |
| Final(% initial) | 108.0 ± 7.7 | 108.9 ± 10.2 | 110.7 ± 9.70 |
| Number of Tumours[c] | 8.50 ± 3.87 | 13.8 ± 4.83 | 16.9 ± 9.85 |
| Tumour Area[d] | 32.18 ± 13.69 | 47.35 ± 14.02 | 78.15 ± 31.19 |

[a]Mean of 10 mice per group ± Standard Deviation.
[b]Among dietary groups there was no statistically significant difference in initial body weight or in the body weight reached after 28 weeks.
[c]Whey Protein versus Casein P = .0138
Whey Protein versus Purina P = .0208
[d]Whey Protein versus Casein P = .0236
Whey Protein versus Purina P ≤ .001
Purina versus Casein P = .0104

TABLE 7

Time at which 55% of mice fed either of three dietary regimen (from 21 months of age to 28 months of age) were dead.

| Dietary treatment | Days of feeding[a] |
|---|---|
| Casein | 92.2 ± 55.2[b] |
| Whey | 125.0 ± 41.6[c] |
| Purina | 92.7 ± 31.7[d] |

[a]Mean of 10 mice per group ± standard deviation.
Survival time for d < c (p < 0.05). If the two control diet groups with near identical survival time are pooled together: b,d < c (p < 0.05).

TABLE 8

VITAMIN CONTENT/100 g DIET

| | Diet 1 | Diet 2 | Diet 3 | Diet 4 | Diet 5 |
|---|---|---|---|---|---|
| Ascorbic acid (vitamin C), mg | 65.0 (N)[a] | 47.0 | 140.0 | 47.0 | 47.0 |
| Niacin, mg | 9.2 | — | — | — | — |
| Riboflavin (vitamin $B_2$), mg | 0.69 (0.60)[b] | 0.54 | 0.54 | 1.00 | 0.54 |
| Thiamin (vitamin $B_1$), mg | 0.63 (0.60)[b] | 0.54 | 0.45 | 0.45 | 1.00 |
| Folic acid, mg | 0.12 | — | — | — | — |
| Vitamin $B_6$, mg | 0.36 | — | — | — | — |
| Biotin, mg | 0.058 | — | — | — | — |
| Pantothenic acid, mg | 3.38 | — | — | — | — |
| Choline, mg | 76.0 | — | — | — | — |
| Vitamin $B_{12}$, mg | 0.55 | — | — | — | — |
| Phylloquinone (vitamin K), mg | 1.8 | — | — | — | — |
| Inositol, mg | 34.39 | — | — | — | — |
| Retinyl palmitate (vitamin A), I.U. | 1800 | — | — | — | — |
| Ergocalciferol (vitamin $D_2$), I.U. | 360 | — | — | — | — |
| Dl-tocopheryl acetate (vitamin E), I.U. | 24.0 | — | — | — | — |

The mineral content of ions or cations (expressed in milligrams per 100 g diet) and the actual chemical compounds fed are:
Ca, 378 ($CaHPO_4.2H_2O$ and $Ca_3(C_6H_5O_7)_2.4H_2O$); P, 208 ($K_2HPO_2.2H_2O$); Fe, 7.7 ($FeSO_4.2H_2O$); Mg. 44 (MgO); Cu, 0.38 ($CuSO_4.5H_2O$); Zn, 2.5 ($ZnSO_4.7H_2O$); Mn 0.63 ($MnSO_4$); Cl, 840 ($C_5H_{14}ClNO$); K, 1050 ($K_2HPO_4.2H_2O$); Na, 245 (NaCl).
[a]N = Not required.
[b] = Values between brackettes are the vitamin concentrations of an adequate mouse purified diet. (AIN 76: KNAPKA J. Jr. in "The mouse in biomedical research". Eds. H. L. Foster, J. D. Small, J. G. Fox, Academic Press, New York, p. 58, 1983).

References Related to Previous and Current Work (Incorporated by Reference)

1) Bounous G., Kongshavn. P. A. L. "The effect of dietary amino acid on immune reactivity"—Immunology 35/257-266/1978

2) Bounous G., Stevenson M. M., Kongshavn P. A. L. Influence of dietary lactalbumin hydrolysate on the immune system of mice and resistance to Salmonellosis—I. of Infect Diseases 144/281/1981

3) Bounous G., Kongshavn. P. A. L. Influence of dietary proteins on the immune system of mice—J. Nutr. 112/1747-1755/1982

4) Bounous G., Letourneau L., Kongshavn. P. A. L. Influence of dietary protein type on the immune system of mice—J. Nutr. 113/1415-1421/1983

5) Bounous G., Kongshavn P. A. L. Differential effect of dietary protein type on the B-Cell and T-Cell immune responses in mice—J. Nutr. 115/1403-1408/1985

6) Bounous G., Shenuda, N., Kongshavn P. A. L., Osmond D. G., Mechanism of altered B-Cell response induced by changes in dietary protein type in mice—J. Nutr., 115/1409-1417/1985

7) Bounous G., Kongshavn P. A. L. Influence of protein type in nutritionally adequate diets on the development of immunity (In press in) "Absorption and utilization of amino acids" Editor, N. Friedman publisher CRC press Fall 1988.

8) Raiha N. C. R., Heinonen K., Rassin D. K., Gaull G. E. Heindnen, Mild protein quantity and quality in low-birth weight infants: 1: Metabolic responses and effects on growth—Pediatric 57/659–674/1976

9) Darling P., Lepage G., Tremblay P., et al Protein quality and quantity in preterm infants receiving the same energy intake. Am. J. Dis. Child 139/186–190/1985

10) Birt D. F., Baker P. Y., Hruza D. S. Nutritional evaluation of three dietary levels of lactalbumin throughout the lifespan of two generations of syrian hamsters—J. Nutrit 112/2151–2160/1982

11) Birt D. F., Schuldt G. H., Salmasi S. "Survival of hamsters fed graded levels of two protein sources'-'—Lab Animal Sci 32/363–366/1982

12) Bounous G., Kongshavn P. A. L., Gold P. "The immunoenhancing property of dietary whey protein concentrate" "clinical and Investigat. Med. 11/271–278/1988.

13) Bounous G., Kongshavn P. A. L., Taveroff A., Gold P. "Evolutionary traits in human milk proteins'-'—"medical hypothesis", 27/133–140/1988.

14) Bounous G., Batist G., Gold P. Immunoenhancing effect of dietary whey proteins in mice: role of glutathione. Accepted for publication in Clin. Invest. Med.

15) Bounous G., Papenburg R., Kongshavn P. A. L., Gold P, Fleiszer D. Dietary whey protein inhibits the development of dimethylhydrazine induce malignancy—Clin./Invert/Med. 11/213–217/1988.

16) Bounous G., Gervais F., Batist G., Gold P. Effect of dietary whey protein and tissue glutathione on the diseases of aging. Submitted to "clinical investigat. med."

17) Farrell H. M., Douglas F. W. Effect of ultra-high-temperature pasteurization on the functional and nutritional properties of milk proteins. Kieler Milch-wirtschfliche Forsch. 35/365–56/1983

We claim:

1. A method of improving the active systemic humoral immune response in a mammal as measured by sheep red blood cell injection (SRBC), comprising administering orally to the mammal an effective amount of undenatured whey protein concentrate (WPC) obtained from bovine, goat or sheep milk and containing substantially all the whey protein present in the raw milk, administered as a daily replacement for up to all the protein consumed by the mammal, wherein the improved active systemic humoral immune response is based on the overall amino acid and associated small peptides pattern resulting from the contribution of substantially all of the WPC protein components, the daily amount of WPC not substantially exceeding the daily protein requirement for the mammal.

2. The method of claim 1, wherein the active systemic humoral immune response in the mammal is characterized by a dose-response pattern with relation to the amount of whey protein concentrate intake by the mammal.

3. The method of claim 1, wherein the improved active systemic humoral immune response is enhanced resistance to pneumococcal infection.

4. The method of claim 1, wherein the whey protein concentrate is undenatured bovine whey protein concentrate.

5. The method of claim 1, wherein the whey protein concentrate is a mixture of bovine, goat or sheep whey protein concentrate.

6. The method of claim 1, wherein the improved active systemic humoral immune response is associated with enhanced resistance of target cells against the mutagenic and carcinogenic effect of dimethylhydrozine.

7. The method of claim 1, wherein the active systemic humoral immune response is measured in splenic lymphocytes during the SRBC driven lymphocyte response.

8. The method of claim 1, wherein the whey protein concentrate has the amino acid composition of

| AMINO ACID | WHEY PROTEIN CONCENTRATE |
| --- | --- |
| Phenylalanine | 3.4 ± 0.3 |
| Tryptophan | 2.1 ± 0.0 |
| Glycine | 2.0 ± 0.2 |
| Serine | 5.2 ± 0.4 |
| Leucine | 10.4 ± 0.7 |
| Isoleucine | 6.1 ± 0.8 |
| Valine | 5.8 ± 0.8 |
| Methionine | 2.1 ± 0.3 |
| Cysteine | 2.3 ± 0.3 |
| Aspartic acid | 10.7 ± 0.7 |
| Glutamic acid | 18.8 ± 0.7 |
| Histidine | 2.0 ± 0.2 |
| Tyrosine | 3.0 ± 0.4 |
| Proline | 6.1 ± 0.7 |
| Arginine | 2.8 ± 0.3 |
| Alanine | 4.9 ± 0.4 |
| Lysine | 9.2 ± 0.5 |
| Threonine | 6.8 ± 1.3 |

9. The method of claim 1, which further comprises orally administering to the mammal about 1.2 to about 1.5 milligrams per day of vitamin B2.

10. The method of claim 1, which further comprises orally administering to the mammal about 0.5 to 0.6 milligrams of vitamin B2 pre 1000 calorie per day.

11. The method of claim 1, which further comprises orally administering to the mammal about 0.5 milligrams per 1000 calorie of vitamin B1 per day.

12. The method of claim 1, which further comprises orally administering to the mammal vitamins B1 and B2 in amounts in excess of the minimum daily requirement for the mammal.

13. A method of producing a sustained increase of tissue concentration level of glutathione in a mammal, which comprises orally administering to the mammal an amount of undenatured whey protein concentrate obtained from bovine, goat or sheep milk and containing substantially all the whey protein present in the raw milk as a daily replacement for up to all the protein consumed by the mammal, wherein the sustained increase of the tissue concentration level of glutathione in the mammal is based on the overall amino acid and associated small peptides pattern resulting from the contribution of substantially all the WPC protein components, the daily amount of whey protein concentrate not substantially exceeding the daily protein requirement for the mammal.

14. The method of claim 13, wherein the sustained increase of tissue concentration level of glutathione in the mammal is characterized by a dose-response pattern with relation to the amount of whey protein concentrate intake by the mammal.

15. The method of claim 13, which further comprises orally administering to the mammal vitamin B2 in an amount of about 0.5 to 0.6 milligrams per 1000 calorie per day.

16. The method of claim 13, wherein the sustained increase of tissue concentration levels of glutathione in the mammal comprises an elevated level of glutathione above normal levels for at least three (3) months.

* * * * *